United States Patent [19]

Kelly et al.

[11] 3,947,382
[45] Mar. 30, 1976

[54] MILDNESS ADDITIVE

[75] Inventors: Ralph Kelly, Cincinnati; Edmond Jean Ritter, Loveland, both of Ohio

[73] Assignee: Cincinnati Milacron, Inc., Cincinnati, Ohio

[22] Filed: Oct. 16, 1973

[21] Appl. No.: 406,955

Related U.S. Application Data

[60] Continuation of Ser. No. 140,604, May 5, 1971, Pat. No. 3,769,242, which is a division of Ser. No. 696,509, Jan. 9, 1968, Pat. No. 3,630,934, which is a continuation-in-part of Ser. No. 613,095, Feb. 1, 1967, Pat. No. 3,538,009.

[52] U.S. Cl. ............... 252/542; 252/89 R; 252/117; 252/525; 252/544; 252/546; 252/548; 260/404.5
[51] Int. Cl.² .... C11D 3/04; C11D 3/30; C11D 3/32
[58] Field of Search ........ 252/546, DIG. 1, 89, 542, 252/548, 544, 545, 117; 260/404.5, 407

[56] References Cited
UNITED STATES PATENTS

| | | |
|---|---|---|
| 2,878,190 | 3/1959 | Dvorkovitz et al. ............... 252/544 |
| 3,166,548 | 1/1965 | Kirkpatrick et al. ............ 252/544 X |
| 3,318,817 | 5/1967 | Smith .............................. 252/544 X |
| 3,538,009 | 11/1970 | Kelly et al. ........................... 252/546 |
| 3,630,934 | 12/1971 | Kelly et al. ........................... 252/547 |
| 3,654,167 | 4/1972 | Akrongold et al. ................. 252/119 |
| 3,769,242 | 10/1973 | Kelly et al. ........................... 252/542 |
| 3,798,182 | 3/1974 | Kelly et al. ........................... 252/546 |
| 3,813,350 | 5/1974 | Kelly et al. ........................... 252/547 |

*Primary Examiner*—Thomas J. Herbert, Jr.
*Attorney, Agent, or Firm*—Plumley & Tyner

[57] ABSTRACT

The degree of skin irritation of detergent compositions is reduced by adding small amounts of compounds having at least two polar groups, e.g. hydroxyl, carboxyl, ester, amino, and amido groups separated by an organic radical of at least 15 carbon atoms which contains a cyclic group. In particular, various aliphatic, aromatic and heterocyclic amino, amido and ester derivatives of polymerized fatty acids are disclosed.

15 Claims, No Drawings

MILDNESS ADDITIVE

This application is a continuation of Ser. No. 140,604 filed May 5, 1971, now U.S. Pat. No. 3,769,242; which is a division of application Ser. No. 696,509, filed Jan. 9, 1968, now U.S. Pat. No. 3,630,934; which is a continuation-in-part of application Ser. No. 613,095 filed Feb. 1, 1967, now U.S. Pat. No. 3,538,009.

The present invention relates to mildness additives which prevent or reduce skin irritation, to compositions which contain a mildness additive that prevents or reduces skin irritation, and to methods for preventing or reducing skin irritation resulting from contact with irritating compositions by modification of the keratin layer of the skin.

A majority of cases of skin irritation can be traced back to a contact of the skin with a chemical composition containing a detergent. This is, in part, due to the nature of the detergent itself and, in part, due to the action of the detergent in weakening the resistance of the skin. Most detergents intrinsically irritate the skin, although the degree of irritation will vary significantly with the detergent. Such irritation can result when the skin is contacted with an aqueous solution of such detergent or when such detergent is retained by a fabric on washing with such detergent which then comes into contact with the skin. As a result of such skin irritation, many otherwise useful detergents are excluded from applications where such detergents come into contact with the skin. In some detergent compositions, e.g. dishwashing liquids and shampoos, a certain degree of skin irritation can be tolerated and is accepted, although not desirable.

The cause for this irritation is not clearly understood, but it is believed that detergents have a denaturing effect on the keratin layer of the skin. As a result thereof, other chemicals which normally do not irritate the skin when combined with a detergent can penetrate the skin and cause irritation. Although numerous attempts have been made to develop additives which reduce or eliminate skin irritation, the additives developed have found only limited success for a very narrow range of detergent compositions.

It is therefore an object of the present invention to prevent or reduce skin irritation resulting from contact of the skin with chemical compositions.

It is another object of the present invention to modify the protein-keratin layer of the skin to prevent or reduce skin irritation when contacted with chemical compositions which irritate the skin.

It is a futher object of the present invention to provide modified compositions used in contact with the skin, in which the modification prevents or reduces skin irritation which would otherwise occur.

It is still another object of the present invention to provide detergent-containing compositions to which a mildness additive has been added which prevents or reduces skin irritation which would otherwise result from the presence of such detergent.

Other objects will become apparent from the following description and claims.

The prevention or reduction in skin irritation is achieved by contacting the skin with a mildness additive having the general formula

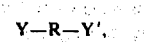

wherein R is a divalent organic radical containing a chain of at least 15 atoms between the open valences of the radical, the majority of which are carbon atoms, and containing a cyclic moiety of at least 5 atoms, and wherein Y and Y' are polar groups; said mildness additive or its salt being soluble or colloidally dispersible in an aqueous phase or organic solvents or other suitable media; the polar groups of the mildness additive being compatible with those of the irritant and stable in aqueous media. The term "dispersible" is meant to define colloidal dispersibility of the mildness additive in concentrations in which the mildness additive is employed in actual use. The term "polar group" is meant to define a group having a dipole moment and containing at least one nitrogen, oxygen, phosphorus, sulfur or combinations thereof. These groups are deemed to be capable of hydrogen bonding with the protein, although the formation of stronger bonds such as covalent bonds is not excluded. The cyclic moiety is preferably a carbocyclic i.e., cyclic hydrocarbon moiety of 5 to 18 carbon atoms which can be saturated or can contain from 1 to 9 double bonds and can contain one or more substituents on the ring. Heterocylic moieties which contain the structures —O—, —S—, —N—, or —NH— in the ring can also be present in the mildness additive and serve as the necessary cyclic moiety. Hetero-atoms are useful.

In accordance with the present invention, it was discovered that skin irritation and other more severe forms of dermatitis caused by the contact of chemicals with skin can be reduced if not eliminated by contacting the skin with a mildness additive as defined above. This reduction or elimination of skin irritations occurs regardless of whether the mildness additive is applied to the skin prior to or simultaneously with the irritating chemical. Rinsing of the skin with water or a mild soap solution after application of the mildness additive but prior to the application of the irritant does not cause a significant change in the effect of the mildness additive when a skin irritant is subsequently applied. This and other types of evidence, such as electrophoretic studies of mixtures of soluble proteins and mildness additives, have shown that some form of interaction occurs between the keratin layer of the skin and the mildness additive. Although the complex formed between protein molecules and the mildness additive can be isolated by the indicated electrophoresis, the specific nature of the complex has not yet been established. It is presumed, however, that both adsorption and some form of chemical interaction are involved. It is further theorized that the cyclic structure in the mildness additive aids in the adsorption of the additive onto the keratin layer of the skin and that the polar groups of the mildness additive interact with the protein molecules of the keratin layer. In addition to the mildness additive containing at least two polar groups, the polar groups of the mildness additive must also be separated by a chain of at least 15 atoms, a majority of which should be carbon atoms. However, the presence of additional polar groups located intermediary to the described two terminal polar groups does not appear to interfere in the mildness effect of the additive. It is believed that as a result of this chain length, the indicated polar groups are capable and do interact with different protein molecules. The irritation of the skin by the action of a detergent or other irritant is believed to be caused by the penetration of the detergent into the skin, causing separation and/or degradation of the protein molecules of the keratin layer, thereby exposing the living cells of the skin to the detergent and, more significantly, exposing these cells to other, more irritating compounds associated with the detergent. The damage to the cells caused by the contact is believed to result in irritation, inflammation, and dermatitis. The mildness additives employed in the detergent compositions of the present invention are believed to counteract this breakdown by providing additional bridges between the protein molecules of the keratin layer, which maintain the integrity of the skin surface thereby preventing the penetration of the detergent molecules through the keratin layer into the living tissue. It is to be understood, however, that we do not wish to be bound by the foregoing explanation of the activity of the mildness additives of the present invention, and that such explanation is only set forth for a better understanding of the present invention.

The mildness additives of the present invention contain at least two polar groups separated by an organic radical of at least 15 atoms, a majority of which are carbon, and which contain a cyclic group. The polar groups should be compatible with the detergent and should be of the type capable of existing in the aqueous phase, i.e. without irreversibly reacting with the water. Additional polar groups may be present in this divalent radical or may be located on branches attached to this radical. Such additional polar groups do not interfere in the effectiveness of the mildness additive. The two polar groups described can be the same or different. Suitable polar groups include hydroxyl (—OH); carboxyl (—COOH); ester (R'O—CO—, wherein R' can be an aliphatic, cycloaliphatic, or aromatic radical of 1–12 carbon atoms, or can be part of a polyester chain), amino (—NH$_2$); substituted amino (NHR'' or —NR''R''', wherein R'' or R''' are aliphatic or aromatic hydrocarbon radicals of 1–12 carbon atoms, or wherein R'' and R''' can combine to form 3- or 6-membered rings with the nitrogen, or wherein R'' is part of a polyamine chain); amido

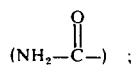

substituted amido

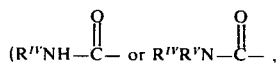

wherein R$^{IV}$ and R$^V$ are aliphatic or aromatic hydrocarbon radicals of 1–12 carbon atoms and R$^{IV}$ can be part of a polyamide chain); quaternary ammonium salts

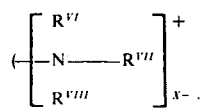

where R$^{VI}$, R$^{VII}$ and R$^{VIII}$ are lower alkyl radicals and X is an anion such as a halogen ion); sulfate (—SO$_4$Me, where Me is a metal and preferably an alkali metal); sulfonate (—SO$_3$Me); sulfonamide (—SO$_2$NH$_2$); substituted sulfonamide (—SO$_2$NHR$^{IV}$ —SO$_2$NR$^{IV}$ or —SO$_2$NR$^{IV}$R$^V$); thio acid salts (—COSMe); thioesters

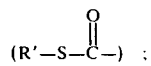

sulfoxides (=SO); sulfonic acid (—SO$_3$H); sulfinic acid (—SO$_2$H); phosphate (—HMePO$_4$ or —Me$_2$PO$_4$); and phosphonium salts (—HPO$_3$Me). The preferred polar groups employed in the mildness additive of the present invention are those which contain, aside from any metal or halogen which may be associated with the polar group in ionic form, carbon and oxygen or carbon and nitrogen. In general functional groups of greater polarity are preferred over those of lesser polarity. It will be apparent that the size of any of the described substituents and particularly hydrocarbon substituents on the polar group will affect the polarity. In general, the preferred substituents on the polar groups are lower alkyl groups and such water-solubilizing groups as polyoxyalkylene radicals, in particular polyethylene glycol chains.

The effectiveness of the mildness additive in preventing skin irritation not only requires the presence of at least two polar groups in the mildness additive but also the separation of the polar groups by an atom chain of at least 15 atoms, the majority of which are carbon atoms. The use of shorter chain lengths does not result in a reduction of the irritating effect of a detergent. The presence of additional polar groups does not interfere in the function of the two polar groups separated by the necessary number of atoms, regardless of whether these polar groups are part of such chain or located on side branches of the molecule. The presence of more than two polar groups each of which are separated by 15 or more atoms increases the effectiveness of a mildness additive in which the polar groups are weak polar groups, such as hydroxyl groups, but does not appear to add significantly to the effectiveness of a mildness additive containing at least two strong polar groups such as carboxyl groups separated by the necessary linking chain.

Although the minimum size of the linking radical is determined by the length of the chain separating the polar groups, the maximum size of the linking radical is determined by the dispersibility of the mildness additive in which it is incorporated. Thus compounds which are not liquid or colloidally dispersible are not suitable in preventing skin irritations. Hence, the upper limit of the size of the linking radical is determined not only by the number of atoms in the linking radical, but also be the presence of additional polar groups in the linking radical which can increase the dispersibility of the mildness additive, as well as the nature of any radical attached to the polar group. In general, however, the linking radical contains less than 80 atoms. As indicated, the linking radical has, preferably, a carbon backbone structure which can be aliphatic, cycloaliphatic, or aromatic in nature. The required carbocyclic or heterocyclic moiety need not be part of the backbone structure. Particularly effective are hydrocarbon linking radicals which contain a cycloaliphatic or aromatic ring structure. In addition to the preferred hydrocarbon structure, the linking radical can also be in the form of polymeric structure such as a polyester, polyether, polyamide, or polyamine. Although other polymeric linking radicals will be apparent to those skilled in the art, many of these radicals are excluded by virtue of the limitations with respect to solubility or collodial dispersibility required to give rise to the mildness-inducing properties. The preferred polymeric linking radicals are the polyether radicals derivable from polyoxyalkylene ethers, containing 2 to 30 oxyalkylene units in which the alkylene radical contains from 2 to 4 carbon atoms. The polyoxyalkylene units can, in addition, contain ester groups. Thus, suitable linking radicals are obtained by the reaction of a polyoxyalkylene glycol with a polycarboxylic acid.

The preferred mildness additives employed in combination with skin irritants are the polymerized, ethylenically unsaturated $C_{12}$–$C_{26}$ fatty acids and polar group-contining derivatives thereof. Generally, the polymerized fatty acids contain from 2 to 4 monomeric acid units, and, consequently, from 2 to 4 carboxyl groups. The polymeric fatty acids can be employed as such as mildness additives or the carboxylic groups can be altered by known chemical reactions into other polar groups, such as by esterification, amidation, and the like. The polymerization of ethylenically unsaturated fatty acids into dimer, trimer, and tetramer acids is known in the art and generally results in a cycloaliphatic ring structure. Thus, the dimer acid derived from linoleic acid has the structure, which can exist in the cis and trans forms, of

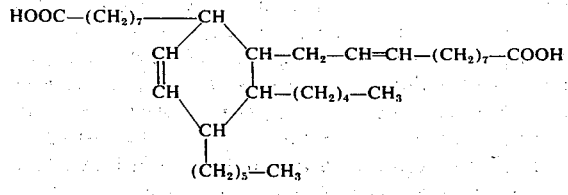

The dimer, trimer, and tetramer acids are commercially available. It will be apparent, in view of the foregoing discussion, that the mildness additive need not be pure, but that a mixture of mildness additives can be employed such as a mixture of dimer and trimer acids, and that the mildness additive can, furthermore, contain compounds which do not add to the mildness properties of the additive such as unpolymerized fatty acids. Various polar groups can be substituted for the carboxyl groups of polymerized fatty acids as described above. Suitable mildness additives which are based on a fatty acid dimer linking radical include the following in which [D] represents the carboxyl-free residue of a dimerized fatty acid and [T] represents the carboxyl-free residue of a trimer acid:

D—(—CH$_2$OH)$_2$
D—(—COOCH$_3$)$_2$
D—(—COOH)$_2$
D—(—CONH$_2$)$_2$
D—(—CH$_2$NH$_2$)$_2$

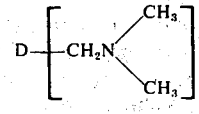

HO—(—CH$_2$—CH$_2$—O)$_m$—CO—[D]—CO$_2$—)$_x$ H
  m=1 to 30; x=1 to 10
D—(—CH$_2$—SO$_4$Na)$_2$
D—(—CH$_2$—SO$_3$Na)$_2$
HOCH$_2$—[D]—COOH
NaOOC—[D]—COONa

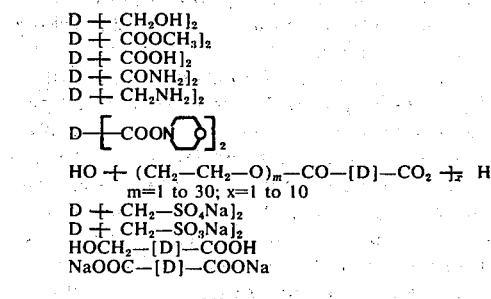

-continued
[D]—(CH$_2$—NH—CH$_2$—CH$_2$—NH$_2$)$_2$
[D]—(CH$_2$—NH—CH$_2$—CH$_2$—CH$_3$)$_2$
D—(—CH$_2$PO(C$_4$H$_9$)$_3$ $^+$Br $^-$)$_2$

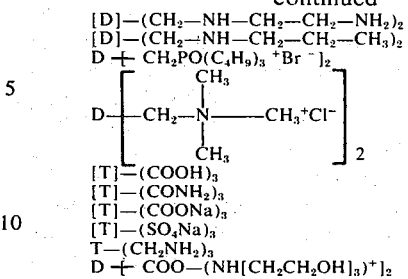

[T]—(COOH)$_3$
[T]—(CONH$_2$)$_3$
[T]—(COONa)$_3$
[T]—(SO$_4$Na)$_3$
T—(CH$_2$NH$_2$)$_3$
D—(—COO—(NH[CH$_2$CH$_2$OH]$_3$)$^+$)$_2$

Other specific mildness additives which are not based on a polymerized fatty acid are cycloaliphatic or aromatic dicarboxylic acids and derivatives thereof which contain at least 15 carbon atoms between at least two polar groups and which are soluble or dispersible. Polymers which are based on repeating cycloaliphatic or aromatic acid moieties and which are soluble or dispersible, are also suitable. Such polymers are, in particular, polymers derived by the reaction of polyoxyalkylene glycols with cyclic dicarboxylic acids such as benzene dicarboxylic acids, dihydrophthalic acids, tetrahydrophthalic acids, cyclohexanedicarboxylic acids. Others include reaction products of such acids with diamines or polyamines. Still another class of suitable compounds includes alkylene oxide addition products to polyols containing cycloaliphatic or aromatic moieties.

The mildness additives described herein above can be employed in combination with any detergent that is anionic, cationic, nonionic, or amphoteric in nature. It will be apparent, however, that the polar groups of the mildness additive should be compatible with those of the detergent to avoid insolubilization of both detergent and additive. The reduction of skin irritation will be observable in all compatible combinations, although the extent of the anti-irritant effect will differ with the various mildness additives discussed, as well as with the detergent. Since some of the detergents, particularly nonionic detergents, are by themselves relatively non-irritating, the described mildness additive is less useful, although the mildness effect of the additive can be established when such detergents, which at normally used concentrations cause little or no skin irritation, are tested at high concentrations and/or longer periods of contact with the skin.

The anti-irritation effect of the mildness additive is exhibited over a wide range of proportions of additive to detergent as indicated above. However, optimum results are generally obtained when the ratio of detergent to mildness additive is in the range of 3:1 to 1:3. This preferred range is applicable regardless of whether the detergent is employed in a dilute or concentrated form.

Anionic detergents which are improved by combination with the described mildness additives include both the soap and the non-soap detergents. Examples of such soaps are the sodium, potassium, ammonium, and alkylolammonium salts of higher fatty acids ($C_{10}$ to $C_{26}$). Non-soap anionic detergents with which the described mildness additives are suitably employed include alkyl sulfates, alkyl sulfonates, alkyl benzene sulfonates, alkyl phenyl polyoxyalkylene sulfonates, alkyl glyceryl ether sulfonates, alkyl monoglyceride sulfates, alkyl monoglyceride sulfonates, alkyl polyoxyethylene ether sulfates, acyl sarcosinates, acyl esters of isothionates, acyl-N-methyl taurides, dialkyl esters of sulfosuccinic acid, and mixtures thereof. In these non-soap detergents, the alkyl or acyl radicals contain from 9 to 20 carbon atoms. As in the soaps, these detergents are employed in the form of sodium, potassium, ammonium, and alkylolammonium salts, as well as similar water-soluble salts. Specific examples include sodium lauryl sulfate, potassium-N-methyl lauroyl tauride, triethanol-ammonium dodecyl sulfonate, potassium polypropylene benzene sulfonate, sodium lauryl sulfonate, dioctyl ester of sodium sulfosuccinic acid, sodium salt of lauryl polyoxyethylene sulfate, and sodium salt of tridecylether polyoxyethylene sulfate.

The cationic detergents which can be reduced in their skin irritation by the addition of the mildness additives of the present invention include, in particular, quaternary ammonium salts which contain at least one alkyl group having from 12 to 20 carbon atoms. Although the halide ions are the preferred anions, other suitable anions include acetate, phosphate, sulfate, nitrite, and the like. Specific cationic detergents include distearyl dimethyl ammonium chloride, stearyl dimethyl benzyl ammonium chloride, stearyl trimethyl ammonium chloride, coco dimethyl benzyl ammonium chloride, dicoco dimethyl ammonium chloride, cetyl pyridinium chloride, cetyl trimethyl ammonium bromide, stearyl amine salts that are soluble in water such as stearyl amine acetate and stearyl amine hydrochloride, stearyl dimethyl amine hydrochloride, distearyl amine hydrochloride, alkyl phenoxyethoxyethyl dimethyl ammonium chloride, decyl pyridinium bromide, pyridinium chloride derivative of the acetyl amino ethyl esters of lauric acid, lauryl trimethyl ammonium chloride, decyl amine acetate, lauryl dimethyl ethyl ammonium chloride, the lactic acid and citric acid and other acid salts of stearyl-l-amido-imidazoline with methyl chloride, benzyl chloride, chloroacetic acid and similar compounds, mixtures of the foregoing, and the like.

Amphoteric, also referred to as ampholytic, detergents which can be improved by the addition of the described mildness additives include alkyl-$\beta$-iminodipropionate, alkyl-$\beta$-aminopropionate, fatty imidazolines, betaines, and mixtures thereof. Specific examples of such amphoteric detergents are 1-coco-5-hydroxyethyl-5-carboxymethyl imidazoline, dodecyl-$\beta$-alanine, the inner salt of 2-trimethylamino lauric acid, and N-dodecyl-N,N-dimethyl aminoacetic acid.

As indicated above, the mildness additives of the present invention can also be employed in combination with nonionic detergent although the beneficial effects of the addition of the mildness additive are less pronounced since nonionic detergents are inherently not as irritating as the above-described detergents. Nonionic detergents include, in particular, the alkylene oxide ethers of phenols, fatty alcohols, and alkyl mercaptans, the alkylene oxide esters of fatty acids, the alkylene oxide ethers of fatty acid amides, the condensation products of ethylene oxide with partial fatty acid esters, and mixtures thereof. The polyoxyalkylene chain in such agents can contain from 5 to 30 alkylene oxide units in which each alkylene unit has from 2 to 3 carbon atoms. Specific examples of nonionic detergents include nonyl phenol polyoxyethylene ether, tridecyl alcohol polyoxyethylene ether, dodecyl mercaptan polyoxyethylene thioether, the lauric ester of polyethylene glycol, the lauric ester of methoxy polyethylene glycol, the lauric ester of sorbitan polyoxyethylene ether, and mixtures thereof.

The mildness additives of the present invention are particularly effective in reducing the irritation caused by such anionic detergents as the alkyl sulfates and sulfonates and the alkyl benzene sulfates and sulfonates, and by such cationic detergents as the described fatty alkyl-containing quaternary ammonium compounds.

Many of the detergents described hereinabove are employed in their commercial applications in combination with builders or other additives, depending on the intended commercial utility of the detergent. The presence of such additives does not affect the ability of the mildness additive to counteract the skin irritation caused by the detergent. As indicated above, it is believed that the skin irritation is caused by the action of the detergent on the skin in causing the keratin of the skin to break down. Although the detergent itself may not be extremely irritating, it allows other materials employed in combination with the detergent which are highly irritating to come in contact with the living tissue of the skin, even though in the absence of the detergent such materials are non-irritating in not being able to break down the keratin of the skin. The mildness additives of the present invention are, therefore, capable of protecting the skin against skin irritation caused by such additives. Builders employed in commercial detergent formulations are generally alkali salts of weak inorganic acids used alone or in admixtures, such as alkali metal, ammonium or substituted ammonium salts of carbonates, borates, phosphates, polyphosphates, bicarbonates, and silicates. Specific examples of such salts are sodium tripolyphosphate, sodium carbonate, sodium tetraborate, sodium pyrophosphate, sodium bicarbonate, potassium bicarbonate, sodium mono- and di-orthophosphate, sodium metasilicate, and mixtures thereof.

The built detergent compositions of the present invention can, furthermore, contain other adjuvants normally employed in detergent compositions such as perfumes, anti-tarnishing agents, anti-redeposition agents, bacteriostatic agents, dyes, fluorescers, fabric softeners, oxygen or chlorine bleaches, suds builders, suds depressors, sequestrants, and the like. The inorganic builders or the combination of the builders and the adjuvants described can constitute up to 80% of the built detergent composition, the remainder of the built detergent composition being the detergent and the mildness additive.

The detergent compositions of the present invention include laundry detergents, kitchen detergents, shampoos, industrial detergents, and the like. The use of the mildness additive of the present invention does not affect the effective concentrations of the detergent, and hence concentrations of detergents heretofore employed are also applicable in the modified compositions of the present invention.

The use of the mildness additive is, however, not limited to unbuilt or built detergent compositions. The additive can be employed in any compositions in which a detergent of the type described is employed in the presence of other materials which may cause skin irritation such as, in particular, in lubricants containing inorganic salts, a particular example of which are cutting fluids. The protection against skin irritations is further not limited to detergents and extends to a wide variety of skin irritants, including such as are contained in deodorants, disinfectants, polishes, hair preparations, cleaning compositions, etc. The irritant can be inorganic in nature, or organic. In view of the foregoing explanation, this is not surprising since the protection derived from the mildness additive is based on the interaction of such with the keratin layer of the skin and not on interaction with the irritant. Because of this interaction, it is furthermore unnecessary to combine the mildness additive with the irritant in order to achieve the protection of the skin. Thus, the mildness additive can be applied to the skin prior to any contact with an irritant and will protect the skin against subsequent irritation for a long period of time.

In establishing the irritations and the mildness effect of the additive, the skin is contacted by immersion or other means with a solution containing the irritant with and without the mildness additive under standardized conditions more specification described below. The principal test employed in the data presented below is an animal immersion test using female, albino guinea pigs. The animal, weighing about 300 to 325 g, is immersed up to the thoracic region in the test solution at 40°C for 4.5 hours per day on 3 successive days. Each animal is thoroughly rinsed and dried after each immersion. Three days after the last immersions, the skin of each animal is examined for gross changes, and grades are assigned which represent the degree of damage to the skin. In general, three animals are tested simultaneously in the same solution. The grading system is based on a scale of 1 to 10, in which the numbers have the following meanings:

| Grade or Rating | Gross Reaction | Skin Damage |
|---|---|---|
| 1 | Severe cracking and bleeding; death of animal in most instances | Extremely severe; death of skin tissue |
| 2 | Severe cracking; moderate bleeding | " |
| 3 | Severe cracking; slight to moderate bleeding | Severe |
| 4 | Moderate cracking | " |
| 5 | Slight cracking | Moderate |
| 6 | Severe scaling | " |
| 7 | Edema; slight to moderate scaling | " |
| 8 | Slight scaling and moderate edema | Slight |
| 9 | Slight redness and edema | " |
| 10 | Normal | Normal |

Despite the fact that this exposure test is conducted using extremely dilute solutions, it is an exaggerated test, as compared to human exposure; although it has been established (see Can. Patent No. 639,398) that the test correlates extremely well with the skin irritation effect observed on human skin.

In preparing the test solution, a 100 g concentrate is first prepared which is then employed in the test solution in 1% by volume concentrations. In order to prepare a homogeneous concentrate which is readily dilutable, the following additional ingredients were added as indicated: Igepal CA-630, a commercially available nonionic wetting agent of octylphenoxypoly(oxyethylene)ethanol; triethanol amine, and capric acid. The triethanol amine (TEA) is employed to allow salt formation of mildness additives employed in combination with anionic detergents and the capric acid (Cap. A.) is employed for the same purpose in combination with cationic detergents. In general, the detergent and the mildness additive are each employed in the examples illustrated below in a concentration of 15 weight percent based on the described 100 g concentrate. Where a built detergent is employed, the amount of detergent is accordingly adjusted to take into consideration the lower active detergent concentration.

The following examples illustrate the effect of the mildness additives of the present invention on skin irritation caused by detergents, using the above-described test.

EXAMPLES 1 to 12

The detergent employed in this series of tests was an alkyl benzene sulfonate having the formula

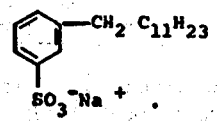

The detergent was employed in 100% active form or in 87% active form, the latter form containing sodium sulfate. The mildness additives employed in this series comprised the dimer of linoleic acid, commercially available as EMPOL 1022, and derivatives of the dimer acid. The dimer acid contained 2–5% of unpolymerized linoleic acid and 19–22% of trimer acid. The dimer ester was prepared from the dimer acid by esterification with a polyethylene glycol having a molecular weight of 400 in a molar ratio of acid-to-polyether of 1:1.25 until an acid number of 5 was obtained. The dimer amide employed is the reaction product of one mole of dimer acid with 4 moles of diethanol amine. The dimer morpholide employed is the reaction product of 4 moles of morpholine with one mole of dimer acid. The dimer amine employed is a commercially available compound in which the carboxyl groups of the dimer acid are replaced by amino methyl ($-CH_2NH_2$) groups. Table I illustrates the results obtained employing the above-described test. The actual composition of the solution to which the animals were exposed is shown. The remainder of the composition of the test solution not indicated in the table was water.

TABLE I

| | Alkyl Benzene Sulfonate Exposure | | | | | | | | |
|---|---|---|---|---|---|---|---|---|---|
| | Detergent | | Dimer Additive | | Other Additive | | | | Ratio of Detergent |
| Example No. | % Concentration | % Active | Type | % Concentration | Type | % Concentration | Average Rating | Improvement in Rating | to Mildness Additive |
| 1 | 0.15 | 87 | — | — | Igepal | 0.05 | 4 | — | — |
| 2 | 0.15 | 87 | Acid | 0.15 | Igepal | 0.016 | | | |
| | | | | | TEA | 0.034 | 9 | 5 | 1:1 |
| 3 | 0.15 | 87 | Ester | 0.15 | Igepal | 0.05 | 8+ | 4+ | 1:1 |
| 4 | 0.15 | 87 | Amide | 0.15 | Igepal | 0.05 | 9 | 5 | 1:1 |
| 5 | 0.15 | — | — | — | — | — | Death | — | — |
| 6 | 0.15 | 87 | Acid | 0.15 | TEA | 0.10 | 7+ | 7+ | 1:1 |
| 7 | 0.176 | 100 | — | — | — | — | Death | — | — |

TABLE I-continued

Alkyl Benzene Sulfonate Exposure

| Example No. | Detergent % Concentration | % Active | Dimer Additive Type | Dimer Additive % Concentration | Other Additive Type | Other Additive % Concentration | Average Rating | Improvement in Rating | Ratio of Detergent to Mildness Additive |
|---|---|---|---|---|---|---|---|---|---|
| 8 | 0.176 | 100 | Acid | 0.15 | TEA | 0.10 | 8 | 8 | 1:1 |
| 9 | 0.176 | 100 | Ester | 0.15 | — | — | 8+ | 8+ | 1:1 |
| 10 | 0.176 | 100 | Amide | 0.15 | — | — | 9 | 9 | 1:1 |
| 11 | 0.176 | 100 | Morph. | 0.15 | TEA | 0.05 | 8+ | 8+ | 1:1 |
| 12 | 0.15 | 87 | biamine | 0.15 | Igepal | 0.10 | | | |
| | | | | | Cap. A. | 0.15 | 9 | 5 | 1:1 |

EXAMPLES 13 to 32

The tests and determination of results illustrated in Examples 1–12 were repeated using sodium lauryl sulfate instead of the alkyl benzene sulfonate. The results are illustrated in Table II.

TABLE II

Sodium Lauryl Sulfate Exposure

| Example No. | Detergent % Concentration | % Active | Dimer Additive Type | Dimer Additive % Concentration | Other Additive Type | Other Additive % Concentration | Average Rating | Improvement in Rating | Ratio of Detergent to Mildness Additive |
|---|---|---|---|---|---|---|---|---|---|
| 13 | 0.15 | 100 | — | — | Igepal | 0.05 | 3 | — | — |
| 14 | 0.15 | 100 | Acid | 0.15 | Igepal | 0.016 | | | |
| | | | | | TEA | 0.034 | 7 | 4 | 1:1 |
| 15 | 0.15 | 100 | Ester | 0.15 | Igepal | 0.05 | 8— | 5— | 1:1 |
| 16 | 0.15 | 100 | Amide | 0.15 | Igepal | 0.05 | 7 | 4 | 1:1 |
| 17 | 0.15 | 100 | Acid | 0.10 | Igepal | 0.016 | | | |
| | | | | | TEA | 0.024 | 6+ | 3+ | 3:2 |
| 18 | 0.15 | 100 | Ester | 0.10 | Igepal | 0.05 | 7— | 4— | 3:2 |
| 19 | 0.15 | 100 | Amide | 0.10 | Igepal | 0.05 | 7 | 4 | 3:2 |
| 20 | 0.15 | 100 | Acid | 0.20 | Igepal | 0.016 | | | |
| | | | | | TEA | 0.044 | 7 | 4 | 3:4 |
| 21 | 0.15 | 100 | Ester | 0.20 | Igepal | 0.05 | 8 | 5 | 3:4 |
| 22 | 0.15 | 100 | Amide | 0.20 | Igepal | 0.05 | 7+ | 4+ | 3:4 |
| 23 | 0.1305 | 100 | — | — | Igepal | 0.05 | 4+ | — | — |
| 24 | 0.1305 | 100 | Acid | 0.15 | Igepal | 0.016 | | | |
| | | | | | TEA | 0.034 | 7 | 3 | 7:8 |
| 25 | 0.1305 | 100 | Ester | 0.15 | Igepal | 0.05 | 8+ | 4 | 1:1 |
| 26 | 0.15 | 100 | — | — | — | — | Death | — | — |
| 27 | 0.15 | 100 | Acid | 0.15 | TEA | 0.10 | 7— | 7— | 1:1 |
| 28 | 0.15 | 100 | Ester | 0.15 | — | — | 7— | 7— | 1:1 |
| 29 | 0.15 | 100 | Amide | 0.15 | — | — | 7 | 7 | 1:1 |
| 30 | 0.15 | 100 | Morph. | 0.15 | TEA | 0.05 | 7+ | 7+ | 1:1 |
| 31 | 0.15 | 100 | Acid | 0.05 | TEA | 0.033 | 5+ | 5+ | 3:1 |
| 32 | 0.15 | 100 | Diamine | 0.15 | Cap. A. | 0.15 | | | |
| | | | | | Igepal | 0.10 | 9 | 9 | 1:1 |

EXAMPLES 33 to 37

The tests and determination of results illustrated in Examples 1–12 were repeated using a soap detergent, i.e., the triethanol amine salt of lauric acid. Although the detergent is relatively mild at a 1% of concentrate level, i.e., 0.15% in test solution, the mildness effect of the additive is particularly shown when the detergent is employed in higher concentrations. The results are illustrated in Table III.

TABLE III

TEA — Laurate Exposure

| Example No. | Detergent % Concentration | % Active | Dimer Additive Type | Dimer Additive % Concentration | Other Additive Type | Other Additive % Concentration | Average Rating | Improvement in Rating | Ratio of Detergent to Mildness Additive |
|---|---|---|---|---|---|---|---|---|---|
| 33 | 0.15 | 100 | — | — | TEA | 0.06 | 7+ | — | — |
| 34 | 0.15 | 100 | Acid | 0.15 | TEA | 0.15 | 8+ | 1 | 1:1 |
| 35 | 0.15 | 100 | Ester | 0.15 | TEA | 0.063 | 9— | 2 | 1:1 |
| 36 | 0.15 | 100 | Amide | 0.15 | TEA | 0.063 | 9— | 2 | 1:1 |
| 37 | 0.45 | 100 | — | — | TEA | 0.18 | Death | — | — |
| 38 | 0.45 | 100 | Acid | 0.45 | TEA | 0.45 | 7+ | 7+ | 1:1 |

EXAMPLES 39 and 40

The tests and determination of results illustrated in Examples 1–12 were repeated using a commercially available amphoteric detergent "Deriphat" 151 C containing N-coco-β-aminopropionic acid. The active component of the detergent was 70%; it was employed in the concentrate in a concentration of 23.2%. A 2% (containing 0.46% of the Deriphat 151 C) test solution caused the deaths of the animals in the described immersion test. When dimer acid (0.15% of test solution) and triethanol amine (0.10% of test solution) were added, the rating of skin irritation improved to an average of 9.

EXAMPLES 41 and 42

The tests and determination of results illustrated in Examples 1–12 were repeated using a commercially available amphoteric phenolic detergent commercially available as "Amphicide" 50 containing in 75% concentration the following active components:

1 Part of the sodium salt of 2-[(2-hydroxy-5-nonylbenzene)methylamino]ethane sulfonic acid, and 3 Parts of the sodium salt of 2-[(3-dimethylaminomethyl-2-hydroxy-5-nonylbenzyl)methylamino]ethane sulfonic acid.

The concentrate contained 22.5% of the Amphicide and was employed as a 2% test solution containing 0.45% Amphicide and resulted in an average rating of 5. The average rating was improved to 9 by the addition of 0.15% of dimer acid and 0.10% of triethanol amine to the test solution.

EXAMPLES 43 to 46

The tests and determination of results illustrated in Examples 1–12 were repeated using "Orvus" AB, a commercially available linear alkane sulfonate detergent containing 40% of a linear alkane sulfonate, 43% of sodium sulfate, and 15% of sodium chloride. The following results were obtained (Table IV).

TABLE IV

Alkane Sulfonate Exposure

| Example No. | Detergent % Concentration | % Active | Dimer Additive Type | % Concentration | Other Additive Type | % Concentration | Average Rating | Improvement in Rating | Ratio of Detergent to Mildness Additive |
|---|---|---|---|---|---|---|---|---|---|
| 43 | 0.375 | 40 | — | — | — | — | Death | — | — |
| 44 | 0.375 | 40 | Acid | 0.15 | TEA | 0.10 | 7 | 7 | 1:1 |
| 45 | 0.375 | 40 | Ester | 0.15 | TEA | 0.02 | 8 | 8 | 1:1 |
| 46 | 0.375 | 40 | Amide | 0.15 | — | — | 7 | 7 | 1:1 |

EXAMPLES 47 to 50

The tests and determination of results illustrated in Examples 1–12 were repeated using Orvus K, a commercially available modified ammonium lauryl sulfate detergent containing an amide builder having the following composition:

| | |
|---|---|
| Alkyl sulfate | 37.5% |
| Alkanol amide | 9.2% |
| Unsulfated alcohol | 1.2% |
| Ammonium sulfate | 0.9% |
| Ammonium chloride | 1.0% |
| Denatured ethyl alcohol | 20.0% |

The following results were obtained (Table V).

TABLE V

Ammonium Lauryl Sulfate Exposure

| Example No. | Detergent % Concentration | % Active | Dimer Additive Type | % Concentration | Other Additive Type | % Concentration | Average Rating | Improvement in Rating | Ratio of Detergent to Mildness Additive |
|---|---|---|---|---|---|---|---|---|---|
| 47 | 0.40 | 37.5 | — | — | — | — | 6 | — | — |
| 48 | 0.40 | 37.5 | Acid | 0.15 | TEA | 0.10 | 9− | 3− | 1:1 |
| 49 | 0.40 | 37.5 | Ester | 0.15 | — | — | 8 | 2 | 1:1 |
| 50 | 0.40 | 37.5 | Amide | 0.15 | — | — | 9− | 3− | 1:1 |

EXAMPLES 51 to 54

The tests and determination of results illustrated in Examples 1–12 were repeated using "Standpol" ES-2, a commercially available 26% active detergent containing the sodium salt of lauryl $C_{12}$ through $C_{14}$ diether sulfate. The following results were obtained (Table VI).

TABLE VI

Lauryl Diether Sulfate Exposure

| Example No. | Detergent % Concentration | % Active | Dimer Additive Type | % Concentration | Other Additive Type | % Concentration | Average Rating | Improvement in Rating | Ratio of Detergent to Mildness Additive |
|---|---|---|---|---|---|---|---|---|---|
| 51 | 0.5718 | 26 | — | — | — | — | 5 | — | — |
| 52 | 0.5718 | 26 | Acid | 0.15 | TEA | 0.10 | 8+ | 3+ | 1:1 |
| 53 | 0.5718 | 26 | Ester | 0.15 | — | — | 8+ | 3+ | 1:1 |
| 54 | 0.5718 | 26 | Amide | 0.15 | — | — | 8+ | 3+ | 1:1 |

EXAMPLES 55 to 58

The tests and determination of results illustrated in Examples 1–12 were repeated employing a cationic detergent commercially available as "Hyamine" 2389 containing 40% methyldodecylbenzyl trimethyl ammonium chloride, 10% methyldodecylxylylene-bis(trimethylammonium chloride), and 50% water, and therefore determined to be 50% active. Test solutions containing 0.30% of the detergent in the absence and in the presence of 0.15% of the below-listed dimer derivatives were prepared and tested in the described immersion test. The following results were obtained in which [D]

represents the carboxyl-free residue of the dimer acid.

| Example | Additive | Average Rating |
|---------|----------|----------------|
| 55 | — | Death |
| 56 | D—(CH₂NH₂)₂ | 7 |
| 57 | D[—CH₂N(CH₃)₂]₂ | 6 |
| 58 | [D]—(CH₂—NH—CH₂—CH₂—CH₂—NH₂)₂ | 7 |

EXAMPLES 59 to 62

The tests and determination of results illustrated in Examples 1–12 and 13–16 were repeated using a dimer glycol and a dimer sulfate as the mildness additive. The following results were obtained:

| Example | Detergent | Mildness Additive | Average Rating |
|---------|-----------|-------------------|----------------|
| 59 | Alkylbenzene sulfonate | Dimer glycol D—[CH₂OH]₂ | 8 |
| 60 | " | Dimer sulfate D—[CH₂—SO₄Na]₂ | 8 |
| 61 | Sodium lauryl sulfate | Dimer glycol | 7+ |
| 62 | " | Dimer sulfate | 9 |

EXAMPLE 63

To a 1% solution of a shampoo commercially available as "Prell" was added 2% by weight of the solution of the triethanol amine salt of the dimer acid of Examples 1–12. Using the above-described exposure test, a rating of 7 was obtained. In the absence of the mildness additive the animals exposed died.

EXAMPLE 64

A cutting fluid containing, per 100 parts of the solution, 4 parts of the dimer acid ester of Example 3, 8 parts of sodium nitrite, 10 parts of triethanol amine, and 1.5 parts of oleyl diethanol amide was employed in the above-described exposure test. A rating of 8+ was obtained for the cutting fluid when tested at 17% concentration. In the absence of the dimer ester the rating dropped to 4.

EXAMPLES 65 to 86

The tests and determination of results illustrated in Examples 1 to 6 and 13 to 16 for anionic surfactants and in Examples 55 to 58 for cationic surfactants were repeated using the indicated mildness additive and surfactants in a concentration of 1%. The following results were obtained:

TABLE VII

| EXAMPLE | Sodium Lauryl Sulfate - Alkyl Benzene Sulfonate Exposure MILDNESS ADDITIVE | SURFACTANT | AVERAGE RATING |
|---------|------------------------------------------------|------------|----------------|
| 65 | Ester of Dimer glycol and Dimer acid | SIS* | 7.8 |
| 66 | Amide of Dimer Diamine and capric acid | ABS** | 9.0 |
| 67 | " | SLS | 8.6 |
| 68 | Trimer Acid | SLS | 7.8 |
| 69 | " | ABS | 8.8 |
| 70 | Polyester of tetrahydrophthalic acid and polyoxyethylene glycol (mol wt. 400) n = 3 to 4 [average degree of polymerization] | SLS | 6.5 |
| 71 | Polyester of tetrahydrophthalic acid and polyoxyethylene glycol (Mol Wt. 400) n = 3 to 4 [n = average degree of polymerization] | ABS | 7.2 |
| 72 | Dimer chloride | SLS | 5.5 |
| 73 | " | ABS | 6.8 |
| 74 | Reaction product of Dimer glycol and toluene diisocyanate | SLS | 6.3 |
| 75 | " | ABS | 6.6 |
| 76 | Dimer glycol diacetate | SLS | 7.5 |
| 77 | " | ABS | 5 |
| 78 | Reaction product of dimer acid and (2-hydroxyethyl)-ethylene diamine in mole ratio 1:2 | SLS | 8.3 |
| 79 | Reaction product of dimer acid and (2-hydroxyethyl) ethylene diamine in mole ratio 1:2 | ABS | 8.3 |
| 80 | Polyester of isophthalic acid and polyethylene glycol, (mol wt. 400) n = 3 to 4 | ABS | 8 |
| 81 | " | SLS | 6.3 |
| 82 | Polyester of phthalic anhydride and polyethylene glycol (ml. wt. 400) n = 3 to 4 | SLS | 5.6 |
| 83 | Condensate of hydrogenated dimer acid with ethylene diamine | SLS | 8.9 |
| 84 | " | ABS | 9 |
| 85 | Tetra-butyl-phosphonium salt of dimer acid | Hyamine | 7.5 |
| 86 | H-856 (commercially | | |

TABLE VII-continued

| EXAMPLE | Sodium Lauryl Sulfate - Alkyl Benzene Sulfonate Exposure | | |
|---|---|---|---|
| | MILDNESS ADDITIVE | SURFACTANT | AVERAGE RATING |
| | available polyol esterified with oleic acid and ethoxylated) | SLS | 6.5 |

*SLS = Sodium lauryl sulfate
**APS = Alkyl Benzene Sulfonate of Examples 1 to 12

EXAMPLES 87 to 93

The exposure test illustrated in Examples 1 to 12 was employed sequentially to demonstrate that the mildness additive interacts with the skin to give rise to protection against irritation. Guinea pigs were immersed in a solution of the mildness additive indicated in the table below for a period of 15 minutes. The animals were then removed from the solution and thoroughly rinsed with tap water. The animals were then reimmersed in a solution of the detergent indicated in the table for a period of 2.25 hours and thereafter rinsed and placed in their cages. This procedure was repeated for 3 days and the animals were graded at the end of a 3-day rest. The following results were obtained. In all instances the concentration of the mildness additive and the detergent were 0.15%.

TABLE VIII

| EXAMPLE | Alkyl Benzene Sulfonate - Sodium Lauryl Sulfate Sequential Exposure | | |
|---|---|---|---|
| | MILDNESS ADDITIVE | DETERGENT | AVERAGE RATING |
| 87 | | ABS* | 5.5 |
| 88 | Triethanol Amine Salt of Dimer Acid | ABS | 8.5 |
| 89 | Diethanolamide of Dimer Acid | ABS | 9.0 |
| 90 | Dimer Morpholide | ABS | 9 |
| 91 | Polyester of Dimer Acid and polyethylene glycol (ml. wt. 400); Polyester degree of polymerization n = 3 to 4 | ABS | 8.5 |
| 92 | | SLS** | 6.0 |
| 93 | Triethanolamine salt of Dimer Acid | SLS | 8.0 |

* = Alkyl benzene sulfonate of Examples 1 to 12
** = Sodium lauryl sulfate

The same results are obtained when the animals are exposed to the mildness additive on only the first day and not on the subsequent days. Some reduction in skin irritation is furthermore obtained when the mildness additive is employed after the skin is exposed to the irritant.

EXAMPLE 94

Three aqueous solutions containing respectively 0.08% tributyl tin oxide (TTO), 0.08% TTO and 0.15% triethanol amine salt of dimer acid, (dimer soap), and 0.08% TTO and 0.15% of triethanolamine salt of oleic acid (oleic soap) were prepared. The oleic soap is considered a mild detergent. These solutions were employed in the above described animal exposure tests. The following results were obtained:

| Solution | Rating |
|---|---|
| 0.08% TTO | 5.5 |
| 0.08% TTO + 0.15% oleic soap | Death |
| 0.08% TTO + 0.15% dimer soap | 8.5 |

EXAMPLE 95

The above described animal exposure tests were employed with the below indicated solutions for an exposure time of 4.5 hours. The following results were obtained.

| Solution | | Rating |
|---|---|---|
| Trisodium phosphate | 1.0% | Death |
| Oleic soap | 0.15% | |
| Trisodium phosphate | 1.0% | 8.5 |
| Dimer soap | 0.15% | |

EXAMPLE 96

A prophetic patch test was conducted on twelve persons using the aqueous compositions shown in the table below. Using adsorbent pads 0.125 cc of the test solution were placed in contact with the skin of each the upper right and left arm for a period of 24 hours. The strip was removed and the test area washed with warm tap water. The area was examined after 20 minutes and again after 24 hours. The reaction of the skin was graded and a numerical value assigned to the reaction as follows:

| | |
|---|---|
| No reaction | 0 |
| Questionable erythema | 1 |
| Positive erythema | 2 |
| Intense erythema | 3 |

The added reaction results of all twelve subjects after about 24 hours and 48 hours from the start of the test were as follows:

TABLE IX

| Test No | Composition | Patch Test Concentration in Weight % | After 24 hrs. | After 48 hrs. |
|---|---|---|---|---|
| 1 | Sodium lauryl sulfate | 8 | 20 | 22 |
| 2 | Sodium lauryl sulfate + Triethanolamine salt of Dimer Acid | 8 | 3 | 13 |
| 3 | Sodium lauryl Sulfate | 6 | 15 | 17 |
| 4 | Sodium lauryl sulfate + Triethanolamine salt of Dimer Acid | 6 | 5 | 5 |
| 5 | Sodium lauryl sulfate + Triethanolamine salt of oleic acid | 6 | 15 | 15 |
| 6 | Sodium lauryl sulfate | 4 | 21 | 20 |
| 7 | Sodium lauryl sulfate + Triethanolamine salt of Dimer Acid | 4 | 5 | 7 |

The foregoing examples have illustrated the mildness inducing effect of the mildness additives on the keratin layer of the skin when such is exposed to a skin irritant before, during or after the application of the mildness additive. In many detergent-containing compositions the skin irritation caused by the detergent is compounded by detergent builders or other components present in the composition. The foregoing examples clearly demonstrate that the mildness agents employed in combination with the detergents are particularly effective in reducing skin irritation where the skin irritation is compounded by the presence of other agents, organic or inorganic. In view of the fact that the overall chemical structure of the mildness additives of the present invention is similar to that of a detergent, it will be apparent that the mildness additives of the present invention can be employed in combination with a skin irritating detergent in any environment, i.e., in the presence of any component in which the detergent can exist. The foregoing examples further illustrate that the greatest benefit of the described invention is realized when the mildness additives are combined with detergents or with detergent-containing compositions which cause skin irritation.

In view of the extreme diversity of skin irritants known today, it will be apparent that a demonstration of reduced skin irritation of all detergent compositions with the described mildness additives is not possible. However, such is not deemed necessary and the foregoing examples are deemed sufficient to illustrate the scope of the invention but are not intended to limit the scope of the invention to such.

What is claimed is:

1. A detergent composition consisting essentially of a non-ionic organic detergent and from 0.005 to 10 parts by weight per part by weight of said detergent of a mildness additive comprising
   I. the substituted polymerized product of 2 to 4 molecules of a monomeric $C_{12}$ to $C_{26}$ unsaturated fatty acid, wherein said polymerized product contains a cyclohexene moiety and instead of 2 to 4 carboxyl groups from said fatty acid, radicals selected from the group consisting of $-CH_2NH_2$; $-CH_2NHCH_2CH_2CH_2NH_2$;

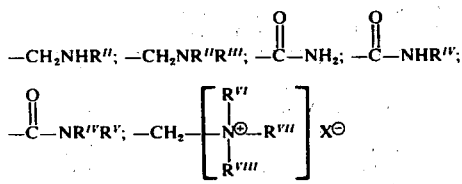

and morpholido; in which $R''$, $R'''$, $R^{IV}$, $R^V$ are aliphatic or aromatic hydrocarbon radicals of 1 to 12 carbon atoms; or where $R''$ and $R'''$ combine to form a 3 to 6 membered ring with the amino nitrogen; $R^{VI}$, $R^{VII}$, and $R^{VIII}$ are lower alkyl radicals and $X^{\ominus}$ is an anion; or II. the saturated products defined in (I); said detergent composition exhibiting reduced skin irritation compared to the same composition absent the mildness additive; said detergent and mildness additive being compatible and stable in aqueous media.

2. The detergent composition of claim 1, wherein said mildness additive is selected from the group designated (I).

3. The detergent composition of claim 1, wherein said mildness additive is selected from the group designated (II).

4. The detergent composition of claim 2, wherein said radicals are $-CH_2NH_2$.

5. The detergent composition of claim 2, wherein said radicals are $-CH_2NHCH_2CH_2CH_2NH_2$.

6. The detergent composition of claim 2, wherein said radicals are

7. The detergent composition of claim 2, wherein said radicals are —CH$_2$NHR$''$.

8. The detergent composition of claim 2, wherein said radicals are —CH$_2$NR$''$R$'''$.

9. The detergent composition of claim 2, wherein said radicals are

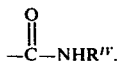
—C(=O)—NHR$^{IV}$.

10. The detergent composition of claim 2, wherein said radicals are

—C(=O)—NR$^{IV}$R$^{V}$.

11. The detergent composition of claim 2, wherein said radicals are

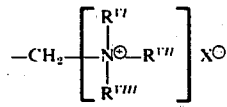

12. The detergent composition of claim 2, wherein said radicals are morpholido.

13. The detergent composition of claim 1, wherein R$^{II}$, R$^{III}$, and R$^{IV}$ are aliphatic hydrocarbon radicals of 1 to 12 carbon atoms.

14. The detergent composition of claim 1, wherein R$''$, R$'''$, R$^{IV}$, and R$^{V}$ are substituted alkyl radicals of 1 to 12 carbon atoms.

15. The detergent composition of claim 1, in which said detergent composition contains from 10 to 80% by weight of the total composition of water soluble inorganic detergent builder.

* * * * *